United States Patent

Matsubara et al.

(10) Patent No.: US 6,579,717 B1
(45) Date of Patent: Jun. 17, 2003

(54) SPECIFIC SOLUTION HANDLING METHOD FOR CALIBRATION AND QUALITY CONTROL BY AUTOMATIC ANALYTICAL APPARATUS

(75) Inventors: Shigeki Matsubara, Hitachinaka (JP); Kyoko Imai, Hitachinaka (JP); Ryuji Tao, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/497,693

(22) Filed: Feb. 3, 2000

(30) Foreign Application Priority Data

Feb. 4, 1999 (JP) .......................................... 11-027914

(51) Int. Cl.$^7$ .............................................. G01N 35/00
(52) U.S. Cl. ............................. 436/50; 436/43; 436/47; 436/48; 436/50; 422/67; 198/343.1; 198/349.5; 198/349.6; 700/266
(58) Field of Search .............................. 422/63, 65, 67; 436/43, 47, 48, 50; 198/343.1, 349.5, 349.6; 700/266

(56) References Cited

U.S. PATENT DOCUMENTS

| | | | | |
|---|---|---|---|---|
| 4,451,433 A | * | 5/1984 | Yamashita et al. | 422/63 |
| 4,678,755 A | | 7/1987 | Shinohara et al. | |
| 5,314,825 A | * | 5/1994 | Weyrauch et al. | 436/43 |
| 5,719,059 A | * | 2/1998 | Mimura et al. | 436/50 |
| 5,730,939 A | * | 3/1998 | Kurumada et al. | 422/67 |
| 5,902,549 A | * | 5/1999 | Mimura et al. | 422/65 |
| 5,989,917 A | * | 11/1999 | McAleer et al. | 436/46 |
| 6,022,746 A | * | 2/2000 | Fritchie et al. | 422/67 |
| 6,080,364 A | * | 6/2000 | Mimura et al. | 422/67 |

FOREIGN PATENT DOCUMENTS

JP          10-339732          12/1998

* cited by examiner

Primary Examiner—Jill Warden
Assistant Examiner—Kathryn Bex
(74) Attorney, Agent, or Firm—Mattingly, Stanger & Malur, P.C.

(57) ABSTRACT

A method for handling specific sample solutions for calibration and quality control by an automatic analytical apparatus in which a sample rack to hold calibrator bottles for required analysis items is set on a rack supply unit by an operator. Identification information of all calibrator bottles on the rack is read out, and data on corresponding calibrator samples are also stored. The operator enters analysis items to be measured, and a measuring channel to be used for calibration. Comparison is made between the planned number of requested calibrations and the number of permissible services to determine whether or not calibrator solution is sufficient. If it is determined to be insufficient, the required number of bottles are displayed according to the difference between the number of permissible services and the number of requests, thereby allowing the operator to add the required number of calibrator bottles. Pressing the analysis start button allows the rack holding the calibrator to be moved to the analysis unit, thereby permitting calibration to be performed.

4 Claims, 8 Drawing Sheets

SPECIFIC SOLUTION HANDLING METHOD FOR CALIBRATION AND QUALITY CONTROL BY AUTOMATIC ANALYTICAL APPARATUS

BACKGROUND OF THE INVENTION

The present invention relates to the method for handling calibrator or control samples in calibration and quality control for automatic analytical apparatus.

Such biological samples as serum, plasma and urine are analyzed by an automatic analytical apparatus. To ensure accurate analysis of many types of analysis items using a great number of samples, it is necessary to perform calibration using the calibrator samples in conformity to these analysis items, and to carry out quality control using the samples for quality control.

Official Gazette of Japanese Patent of Japanese Patent Laid-Open NO. 339732/1998 (TOKKAIHEI) discloses an automatic analytical apparatus with the analysis units laid out along the transfer line, where in the rack holding reference solutions and the rack holding control samples are transferred to the analysis unit to perform calibration and quality control. Calibration and quality control are repeated as required. U.S. Pat. No. 4,678,755 discloses an automatic analytical apparatus where calibration time intervals differ according to the type of analysis items.

SUMMARY OF THE INVENTION

The object of the present invention is to provide a method for handling specific solutions to relieve operators of burdensome work of checking the remaining volume of specific solution such as calibrator or control samples, and to permit highly reliable analysis procedures to be followed.

The present invention uses a rack loaded with one or more bottles to store specific solutions used repeatedly for calibration or quality control. Such a bottle is referred to as a specific bottle, and the corresponding rack is called a specific rack. The specific rack is set on the rack supply unit of the automatic analytical apparatus equipped with an analysis unit for sample analysis. Identification information provided on the specific bottle on the specific rack is read. Based on this information, the number of permissible services for each analysis system is stored in the storage unit with regard to the specific solution in all the specific bottles on the specific rack.

The planned number of times that calibration or quality control is performed is identified for each analysis item by the controller according to the information of request made to the controller. Based on said planned number of times and the number of permissible services stored in the storage unit, the controller determines if specific solution on the specific rack is sufficient or not. If the controller has determined it as insufficient, the number of new specific bottles that must be added is displayed on the screen of the display unit to ensure that the number of said bottles is sufficient for the planned number of times. The rack where new bottles are added is transferred to a specified analysis unit from the rack supply unit, and calibration or quality control are carried out.

In a preferred embodiment, the number of permissible services provided by the remaining specific solution is displayed on the display unit for each specific bottle on the specific rack. The controller determines whether or not the specific bottle set on the rack supply unit is the first bottle not registered previously. Based on the result of this evaluation, the controller manages the term of validity subsequent to opening of the bottle, using a reference time point which is the time when the identification information on said first bottle has been read. The analysis unit where the specific rack is fed is selected through the screen designed to select a combination of the types of analysis items and analysis units.

DESCRIPTION OF THE PREFERRED EMBODIMENT

Figure 1:
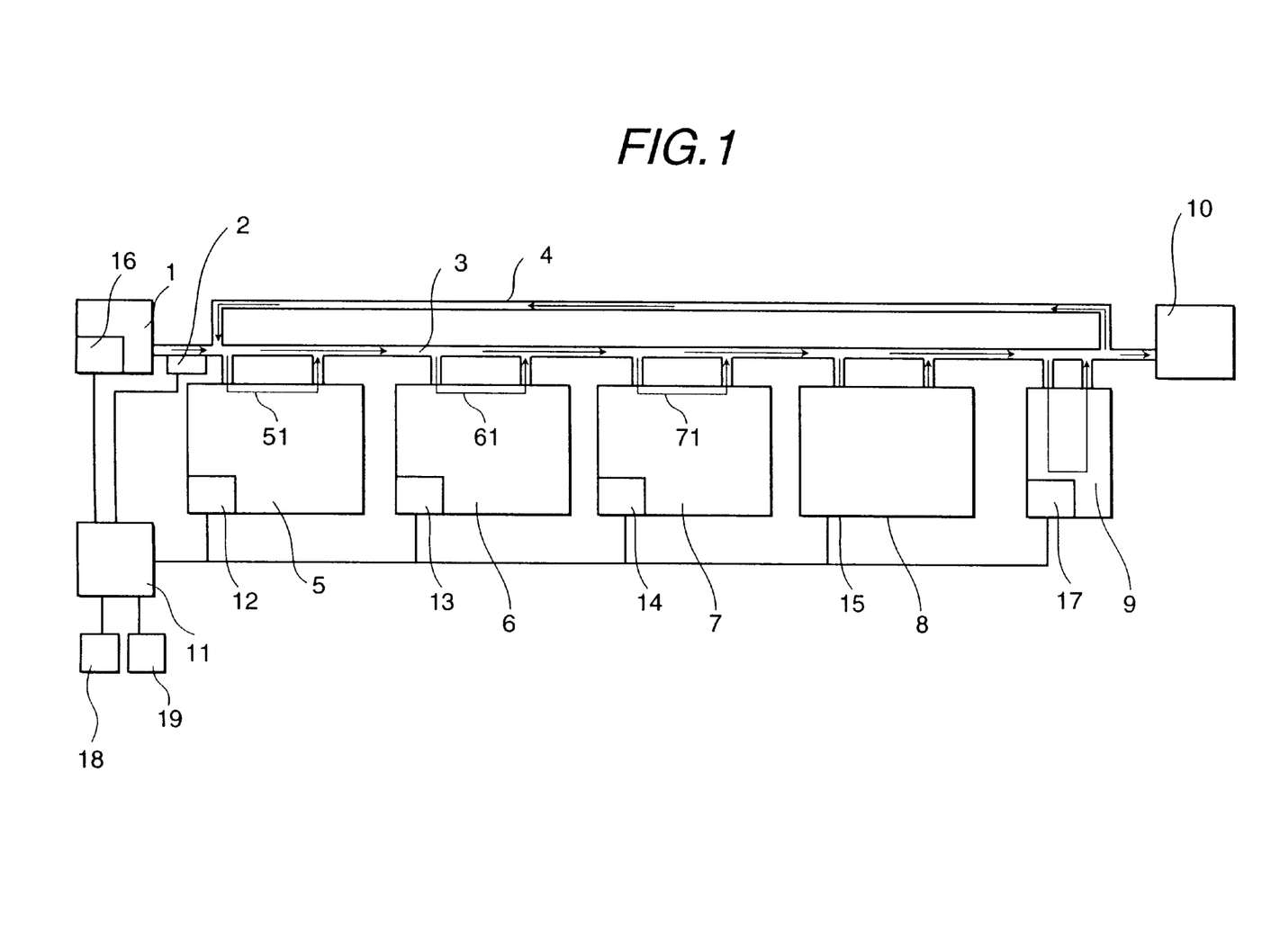
FIG. 1 is a schematic plan view representing an overall configuration of an automatic analytical apparatus as one embodiment of the present invention.

FIG. 1 shows one embodiment of the automated analytical apparatus according to the present invention.

The embodiment in FIG. 1 comprises a sample supply device 1, ID read-out device 2, transfer line 3, return line 4, analysis modules or analysis units 5 to 8, sample rack standby device 9, sample rack collection device 10, and overall management computer 11. In this embodiment, a sample rack storing multiple sample vessels is transferred. It is sufficient if the sample rack to be moved or sample carrier is capable of storing one or more samples.

The sample supply device 1 can accommodate multiple sample racks each holding multiple samples, and supplies each rack to the transfer line 3. Analysis units 5 to 8 are laid out long the transfer line 3 and are connected detachably to the transfer line. The numbers of units is satisfactory if there are one or more immunological analysis units and one or more biochemical analysis units, and any number of units will do. In the illustration, four units are used. Four analysis units 5 to 8 are available in two types of analysis units. Namely, the first type is composed of two analysis units 5 and 6 laid out on the upstream side of the transfer line 3. They are the immunological analysis units to implement immunoassay of many immunological analysis items. The second type is composed of two analysis units 7 and 8 laid out on the downstream side of the transfer line. They are mainly composed of biochemical analysis units used to implement biochemical assay by causing chemical reaction of the many biochemical analysis items.

The transfer line 3 transfers the sample rack from the sample supply device 1 to the required one of the analysis units 5 to 8 in response to the instruction of the control device to ensure that the detection rack having completed fractionation of the sample to that analysis unit is stored into the sample rack collection device 10.

Each of the analysis units 5 to 8 has lead-in lines 51, 61, 71 and 81 to allow access of the sample rack to pick up samples. The sample rack is led into the lead-in lines 51, 61, 71 and 81 inside analysis units 5 to 8 from the transfer line 3 by means of the lead-in mechanism (not illustrated). The return line 4 is used to return to the inlet side of the transfer line 3 the sample rack analyzed by any one of the analysis units 5 to 8, when it must be re-analyzed or must be analyzed by another analysis unit. The sample rack standby device 9 provides a space for temporary standby of the sample rack before the sample rack analyzed by any one of the analysis units is further analyzed by another analysis unit, or before a decision is made to determine whether analysis items should be re-examined or not, following completion of collection of the sample by any one of the analysis units.

The analysis units 5 to 8 are provided with individual computers 12 to 15 to control processing required in each of the units. The sample supply device 1 incorporates a computer 16 to control the operations required in said sample supply device 1, return line 4 and sample rack collection device 10. The sample rack standby device 9 has a computer 17 to control the operations required in the sample rack standby device. These individual computers and ID read-out device 2 are connected to the overall management computer 11. The computer 11 is connected with an operation device 18 to input information required for analysis operation and a display device 19 to display the result of analysis and operation screen. The display operation on the display device is controlled by the computer 11. The control device comprises overall management computer 11 and individual computers 12 to 17.

The sample held by the sample rack is provided with a sample ID (for example, bar code) to show information on the sample (reception number, patient name, requested analysis item, etc.). The sample rack has a rack ID (for example, bar code) showing rack identification information such as rack number. The sample rack fed from the sample supply device 1 is transferred by the transfer line 3. When the sample rack has shifted to the transfer line 3, the sample ID and/or rack ID is read by the ID read-out device 2 (for example, bar code reader) and is fed to the computer 11. Based on the read information, the computer 11 determines the analysis unit which should analyze the requested analysis item of the relevant sample, and gives that information to individual computer 16 and the individual computer of the determined analysis unit.

Let us assume that the same sample rack goes to the immunological analysis unit 5 and biochemical analysis unit 7 from the sample supply device 1, and analyzes the sample held by said sample rack regarding immunological analysis items and biochemical analysis items. The sample rack is fed to immunological analysis unit 5 by the transfer line 3, and is dispensed on the lead-in line 51 to pick up the sample. It is then subjected to immunoassay according to the type of heterogeneous analysis method. Upon completion of dispensing, the sample rack is fed to the biochemical analysis unit 7 by the transfer line 3 if the sample held by said sample rack is not specified to receive automatic re-inspection. In the biochemical analysis unit 7, the sample held by said sample rack is analyzed biochemical analysis items by the homogeneous analysis method. The sample racks holding the samples having been picked up for biochemical analysis are fed for collection to the sample rack collection device 10 by the transfer line 3.

If the sample held by the sample rack is specified for automatic re-inspection, and contains the immunological analysis item specified for automatic re-inspection, said sample rack is fed to the sample rack standby device 9 by the transfer line 3 without making access to other analysis units 6 to 8, after completion of sample pickup for immunoassay. In the sample rack standby device, said sample rack is made to stand by temporarily. During this time, computer 11 makes a decision according to the specified algorithm or logic to determine whether re-inspection is required or not. If the re-inspection is necessary as a result of this decision, the sample rack is fed back to the inlet of the transfer line 3 by the transfer line 3 and return line 4. It is again fed to the analysis unit 5 by the transfer line 3. The sample held by said sample rack is again picked up, and re-inspected for the related analysis item; namely, it is subjected to immunological analysis again. Upon completion of the sample for another immunoassay by immunological analysis unit 5, the sample rack is fed back for collection to the sample rack collection device 10 by the transfer line 3, without making access to the analysis unit 8 and sample rack standby device 9, if the sample held by said sample rack is not specified for re-inspection.

When the sample held by said sample rack is specified for re-inspection and contains the biochemical analysis items specified for re-inspection, the sample rack having been dispensed at the analysis unit 7 will be treated according to the same steps as the sample rack having been dispensed at the analysis unit 5 when the sample held by said sample rack is specified for re-inspection and contains the immunological analysis items specified for re-inspection.

If there is another sample rack to be subjected to biochemical analysis by analysis unit 8 while the sample rack is subjected to immunological analysis by any one of the analysis units 5 to 8, for example, by analysis unit 5, said sample rack may be directly carried to the analysis module 8 from the sample supply device by the transfer line 3, without making access to any of analysis units 5 to 7. In this sense, the transfer line 3 can be called "overtake type transfer line".

Analysis can be made for immunological analysis items and part of biochemical analysis items by the biochemical analysis unit 7 or 8 according to the homogeneous analysis method type. When the same sample is subjected to both biochemical analysis by the biochemical analysis unit and immunological analysis by the immunological analysis unit, analysis by the immunological analysis unit precedes analysis by biochemical analysis unit in this embodiment.

The biochemical analysis unit employs the pipette nozzle which is repeatedly used to pick up samples, while the immunological analysis unit uses the disposable pipette tip to pickup samples. Since priority is given to picking up samples by the immunological analysis unit, it is possible to prevent adverse effect on the result of sample carry-over immunological analysis from the biochemical analysis unit.

Figure 2:
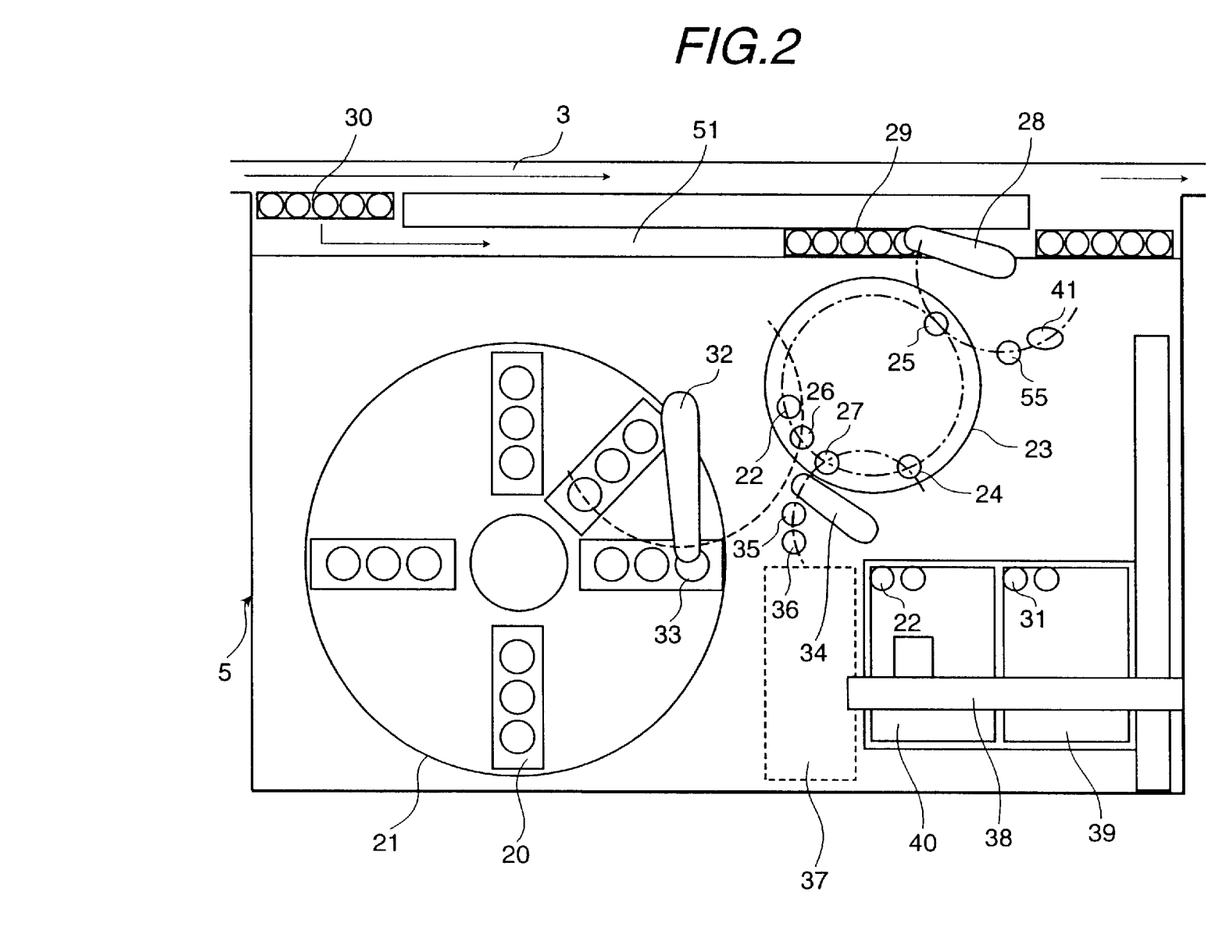
FIG. 2 is a schematic plan view representing the configuration example of the immunological analysis unit of the automatic analytical apparatus shown in FIG. 1.

FIG. 2 shows an example of the detailed configuration of immunological analysis unit 5 of FIG. 1. This immunological analysis unit uses the disposable pipette tip to be replaced for each sample. Analysis is made by heterogeneous analysis method accompanied by B/F separation. Multiple reagent vessels 20 are arranged in a circular form on the reagent disk 21, and the reagent disk 21 is rotated by the motor. Multiple reaction vessels 22 are laid out in a circular form on the reaction disk 23 equipped with a thermostatic bath, and said reaction disk 23 is rotated by a motor. Disposable reaction vessels 22 are moved to the sample discharge position 25 reagent discharge position 26 and reaction solution suction position 27 from the loading system 24 on the reaction disk 23 by this rotation.

The pipetter arm 28 to pick up samples can be rotated and moved by the motor to the sample discharge position 25 from the sample suction position 29 on the lead-in line 51. The sample rack 30 is pulled to the lead-in line 51 from the transfer line 3. Before the sample (specimen) held by said sample rack and positioned at the sample suction position 29 is dispensed into reaction vessels 22 located at the sample discharge position 25, the disposable pipette tip 31 is connected to the bottom end of the connection nozzle held vertically by the arm.

The reagent pipetter arm 32 can be rotated and moved to the reagent discharge position 26 from the reagent suction position 33 on the reagent disk 21.

The sipper arm 34 can move between the reaction solution suction position 27, buffer solution suction position 35 and flow cell washing solution 36. The sipper has a function to feed the reaction solution sucked from a suction nozzle held onto the rotatable arm 34, to the flow cell inside the detection unit 37 through a tube.

The robot arm of the parts transfer mechanism 38 uses the gripping mechanism to carry the disposable pipette tip 31 from the tip storage position 39 to the tip installation position 55, and to carry the disposable reaction vessel 22 from a reaction vessel storage position 40 to the vessel loading system on the reaction disk 23. The reagent pipetter with arm 32 and the sipper with arm 34 can clean their own nozzles at respective cleaning positions (not illustrated).

The following describes the operation of the immunological analysis unit 5. At first, the parts transfer mechanism 38 carries the disposable pipette tip 31 to the tip installation position 55, and the disposable reaction vessel 22 to the vessel loading system 24. When the sample rack 30 to hold the sample to be analyzed is positioned at the sample suction position 29, the pipetter arm 28 to pickup samples connects the pipette tip 31 to the connection nozzle held by itself at the tip installation position. After that, it moves the connection nozzle to the sample suction position to suck the sample inside the pipette tip.

During this time, reagent disk 21 is rotated in such a way that the reagent vessels 20 containing reagent solution used to analyze the relevant sample comes closer to the reagent suction position 33. After the sample is sucked inside the pipette tip 31, the arm 28 moves the pipette tip to the sample discharge position 25, and the sample pickup pipetter discharges the sucked sample into the reaction vessel 22. After that discharge, the arm 28 moves the pipette tip to the tip discard position 41, and the pipette tip is removed from the connection nozzle at that position and is discarded.

The reaction vessel 22 having received the sample on the reaction disk 23 is moved to the reagent discharge position 26 by the rotation of the reaction disk 23 in the counterclockwise direction. The reagent pipetter sucks the reagent solution positioned at the reagent suction position 33 inside the nozzle mounted on the arm 32, and discharges this reagent into the reaction vessel moved to the reagent discharge position 26 on the reaction disk 23. Reagent used for immunological reaction by heterogeneous analysis method includes the solution containing the fine particulate solid phase which can bond the antigen and antibody, fluorophore, enzyme, and solution containing label substances such as chemical luminescent substances which can serve as label. Magnetic particles are preferred solid phase suited for B/F separation.

Until the immunological reaction proceeds sufficiently in the reaction vessel, reaction vessel 22 containing mixed solution is moved one rotation or more by the reaction disk 23, and is positioned to the reaction solution suction position 27 after the lapse of a specified time. The sipper sucks reaction solution from the reaction vessel of the reaction solution suction position 27 through the nozzle attached to the arm 34. Then it moves the nozzle to the buffer solution suction position 35 to suck the buffer solution lead the reaction solution to the flow cell inside the detection unit 37 through the tube.

A magnet is located in the vicinity of the tube loading the flow cell or reaction solution, and magnetic particles as solid phase are captured by magnetic force. Immunological composites bonded with solid phase, namely, bound is separated from the antigen or antibody; that is, B/F separation takes place. When solid phase is captured in the flow cell, the label bonded to the solid phase is measured. When the solid phase is captured in the tube, the label in solution including the free portion is measured. Or a magnet is laid out in the vicinity of the reaction solution suction position 27 on the reaction disk 23, and reaction solution is sucked by the sipper.

In this embodiment, B/F separation is implemented by the tube. Solution including free label is held in the flow cell and analysis result for immunological analysis items is obtained by measuring the chemical luminescence of label substances. After that, the sipper arm 34 positioned its own nozzle at the washing solution bottle 36, and feeds the sucked washing solution to the flow cell, thereby washing inside the flow cell.

The configuration of the immunological analysis unit 6 in FIG. 1 is the same as that shown in FIG. 2. Therefore, its explanation will be omitted to avoid duplication.

Figure 3:
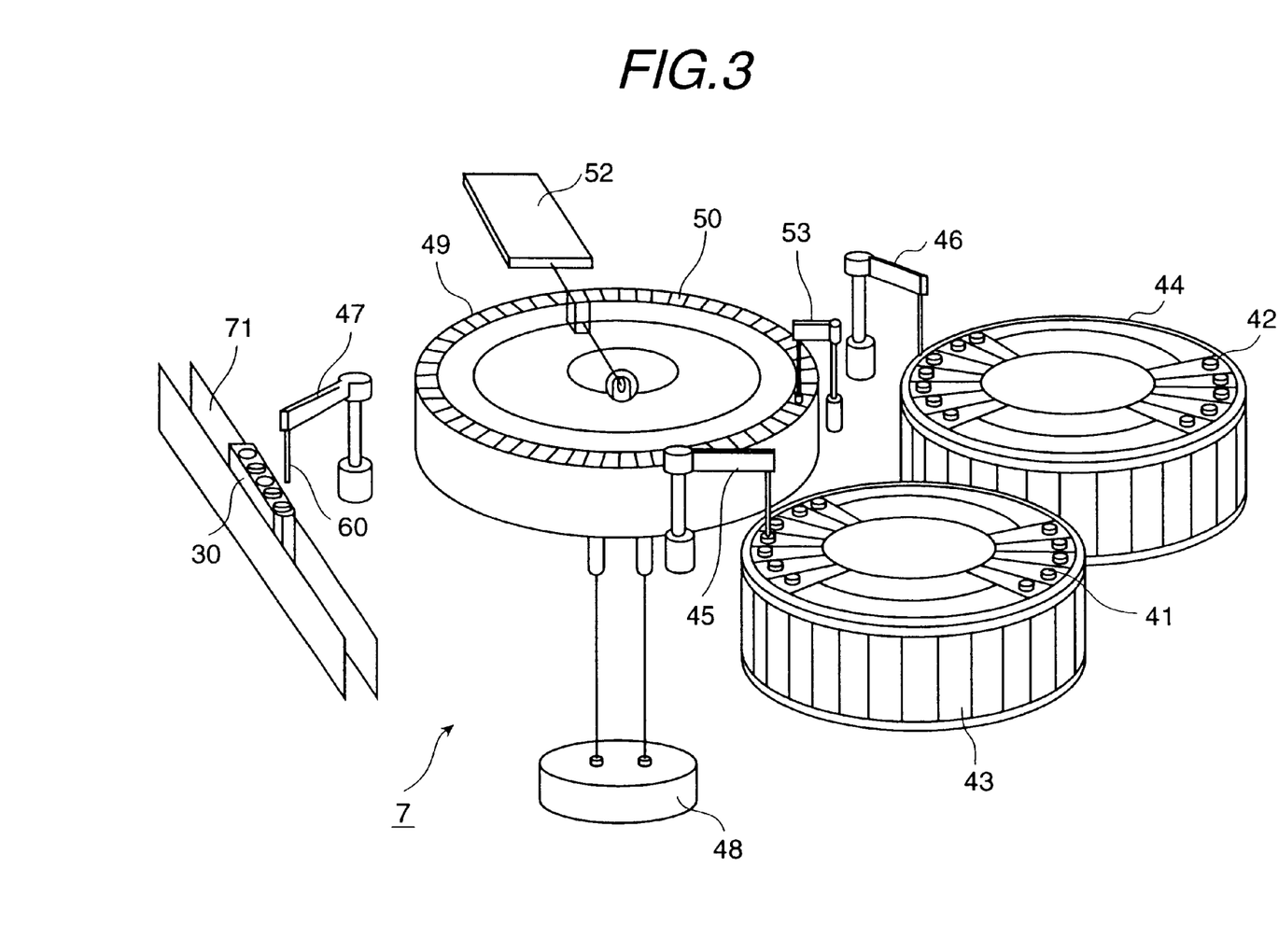
FIG. 3 is a schematic perspective view representing the configuration example of the biochemical analysis unit of the automatic analytical apparatus shown in FIG. 1.

FIG. 3 shows an example of the biochemical analysis unit 7 of FIG. 1. The biochemical analysis unit 7 is provided with (1) a reagent system including 1st and 2nd reagent disks 43 and 44 where multiple 1st reagent bottle 41 and 2nd reagent bottle 42 are laid out in a circular form, and the 1st and 2nd reagent pipetters 45 and 46, (2) a sample system including a pipetter 47 to pick up samples, (3) a reaction system where multiple reaction vessels 50 are arranged on the reaction disk 49 where thermostatic water from the thermostatic bath 48 is circulated, and (4) a measuring system including the multi-wavelength photometer 52.

In the biochemical analysis unit 7, the reaction vessel 50 arranged on the reaction disk 49 is washed by the cleaning mechanism after treatment of each vessel and is used repeatedly. In the pipetter 47 to pick up samples, the pipette nozzle 60 to hold the samples therein is mounted on the rotatable arm. The walls inside and outside the said pipette nozzle are washed at the cleaning position (not illustrated) until dispensation of the next sample is started after dispensation of the previous sample, whereby said pipette nozzle 60 can be used repeatedly despite change of the sample. Said biochemical analysis unit 7 provides analysis for immunological analysis items and biochemical analysis items, according to the homogeneous analysis method without B/F separation during analysis.

The sample held by the sample rack 30 pulled into the lead-in line 71 from the transfer line 3 is sucked into the pipette nozzle 60 by the pipetter 47 at the sample suction position on the lead-in line 71, and is added to the reaction vessel 50 located at the sample discharge position on the reaction disk 49. The reaction vessel 50 having received the sample is moved to 1st reagent discharge position by rotation of the reaction disk 49, where 1st reagent sucked from 1st reagent bottle 41 into said reaction vessel 50 is added to reaction vessel 50 by the 1st reagent pipetter 45. The reaction vessel 50 where 1st reagent is added is fed to the agitation position where the sample (specimen) and 1st reagent are agitated by the agitator 53.

Furthermore, when addition of the 2nd reagent is required, the reaction vessel 50 after agitation is moved to the reagent discharge position, where 2nd reagent sucked from the 2nd reagent bottle 42 is added to the said reaction vessel 50 by the 2nd reagent pipetter 46. The reaction vessel 50 having received 2nd reagent is fed to the agitation position, where the sample added to the reaction vessel 50 and 1st and 2nd reagents are mixed by agitation, thereby forming reaction solution.

The reaction vessel 50 containing the reaction solution is fed to the measuring position, where multi-wavelength absorbance of the reaction solution is measured by multi-wavelength photometer 52, thereby obtaining the result of analysis for biochemical analysis items. In this biochemical analysis unit 7, the immunological, complex generated by immunological reaction in the reaction vessel (e.g. bondage reaction between antigen and antibody) is suspended in the solution; therefore, the result of analyzing the immunological analysis items is obtained by measuring turbidity of the solution with the multi-wavelength photometer 52.

The configuration of the analysis unit 8 in FIG. 1 is the same as that shown in biochemical analysis unit 7 of FIG. 3, except that immunological analysis items are not subjected to analysis. So its explanation will be omitted to avoid duplication.

The channel inside the automatic analytical apparatus covering the range from pipetting of the sample and reagent to measurement of reaction solution thereof is generally called a measuring channel (analysis channel). In the example shown in FIG. 1, each analysis unit incorporates only one measuring channel, but may incorporate more than one measuring channel. Since calibration and control samples are repeatedly used, they are stored in bottles to ensure that the capacity thereof is sufficient for use a multiple number of times.

Whether in biochemical assay, immuno assay or other types of assay, the automatic analytical apparatus performs calibration using reference samples for calibration, namely, calibrator samples (calibrators). Based on the result of said calibration, the sample to be analyzed is made to react with the reagent, and reaction solution thereof is measured. Calibration is carried out for each analysis item (analysis component), using two or more types of calibrator samples having different concentrations. Furthermore, even if the same analysis item having the same concentration is analyzed, different calibration curves are obtained when the measuring channel is different. This makes calibration different for each measuring channel. Calibration is performed according to the type of the analysis item at specified time intervals, for example, every hour, every week, every time the reagent is replaced, or when a change has occurred to the measuring channel.

To ensure a continuous long-time analysis of biochemical samples, it is important to check the remaining volume of calibrator samples and quality control samples. Use of the present invention provides automatic management of the remaining volume of specific solutions such as calibrator samples and/or quality control samples. Consequently, it relieves the operator of burdensome work. It also serves to avoid calibration or quality control failure resulting from human errors, and to minimize the waste of precious specific solution.

Figure 4:
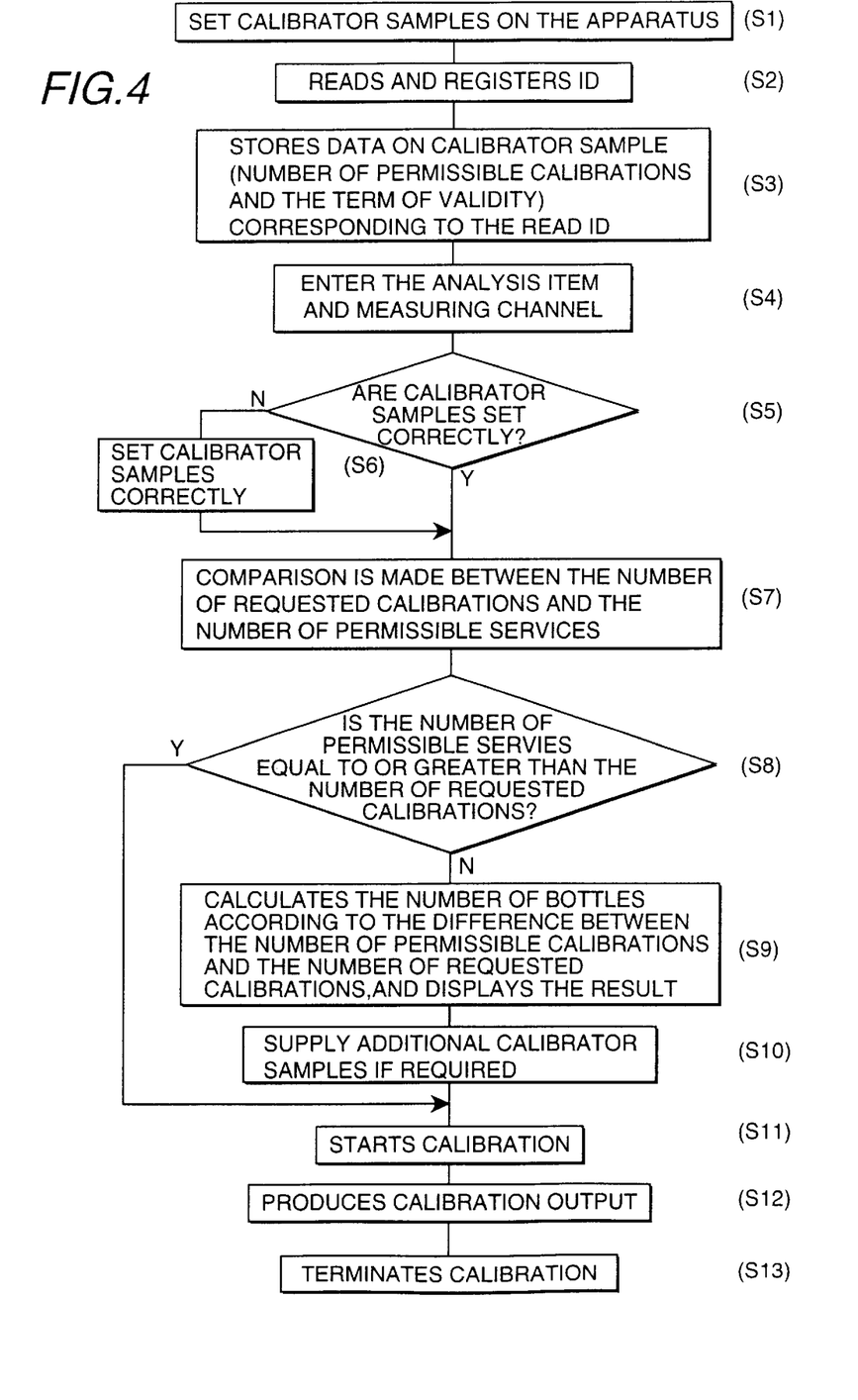
FIG. 4 is a flow chart representing the calibration procedure to start analysis operation.

FIG. 4 is a flow chart representing the calibration procedure to start analysis operation using the automatic analytical apparatus shown in FIG. 1. The remaining volume of calibrator samples are managed in this operation process.

In Step S1, the operator mounts the calibrator bottle accommodating calibrator samples on the sample rack for calibration where in said bottle is open. The number of bottles mounted on this rack is one or more. It is preferred that multiple bottles accommodating the solution containing the analysis items of one type be mounted on one rack. Since multiple types of analysis items are contained in one solution, one bottle can be used in common for several types of analysis items. The bottles mounted on the rack may be either sealed or already opened. Then the operator sets the calibrator rack on rack supply unit 1 of the automatic analytical apparatus.

In Step S2, identification information (ID), similar to the barcode attached to the calibrator bottle, is read by barcode reader 2 mounted on the rack supply unit 1 before the calibrator rack moves to transfer line 3. At this time, identification information of all the calibrator bottles on the same rack is read. The information thereof is sent to computer 11. If the bottle is not registered before this read operation, namely, if the identification information of said bottle is not stored in the memory device of the computer, the computer 11 determines that the date for bottle opening is the date when said bottle is set on the rack supply unit 1. Namely, for the bottle having the ID read out for the first time by the automatic analytical apparatus, the term of validity subsequent to its opening is managed by the computer 11, starting from the date of reading. The computer registers the bottle sequence number and bottle opening date by storing them into the memory device. If the read bottle number is already stored, it is not registered again; the number of dates elapsed subsequent to the previous opening date is the object to be managed for the term of validity.

The identification information provided on each calibrator bottle includes such information items as the term of validity prior to bottle opening, the term of validity subsequent to bottle opening, bottle sequence number, production lot number, bottle size, number of permissible services and analysis item code.

In Step S3, the computer 11 stores the number of permissible services for each analysis item into the memory device for calibrator solution in all the bottles on the rack according to the identification information provided on each calibrator bottle on the rack. Namely, said computer stores and registers the term of validity prior to bottle opening, the term of validity subsequent to bottle opening, the number of permissible services of the unused calibrator sample, etc.

Figure 6:
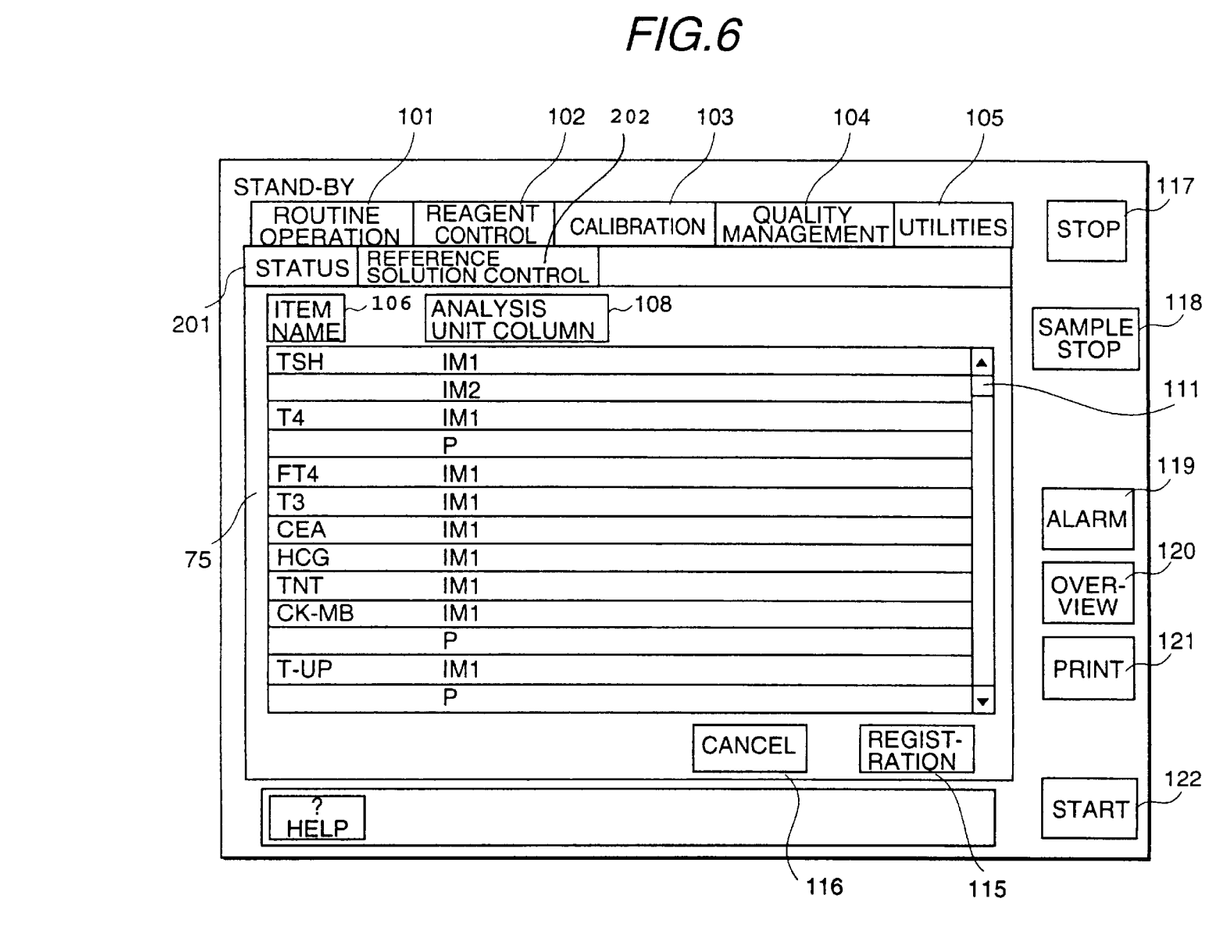
FIG. 6 represents an example of the screen used to select an analysis unit and analysis item.

In Step S4, the operator operates the operation unit 18 and enters into the computer 11 through the screen shown in FIG. 6 the analysis item to be measured for calibration and the measuring channel to be used for this purpose. This information is stored in the memory device and is registered.

In Step S5, the computer 11 checks to see whether or not calibrator samples required for analysis items are correctly set on the rack supply unit 1 according to the data entered so far. To put it specifically, it checks for correct setting of all multiple calibrator bottles of different concentrations required for each analysis item, namely, calibrator bottles of low and high concentrations. If said bottles are not correctly set, set them correctly according to Step S6.

Figure 5:
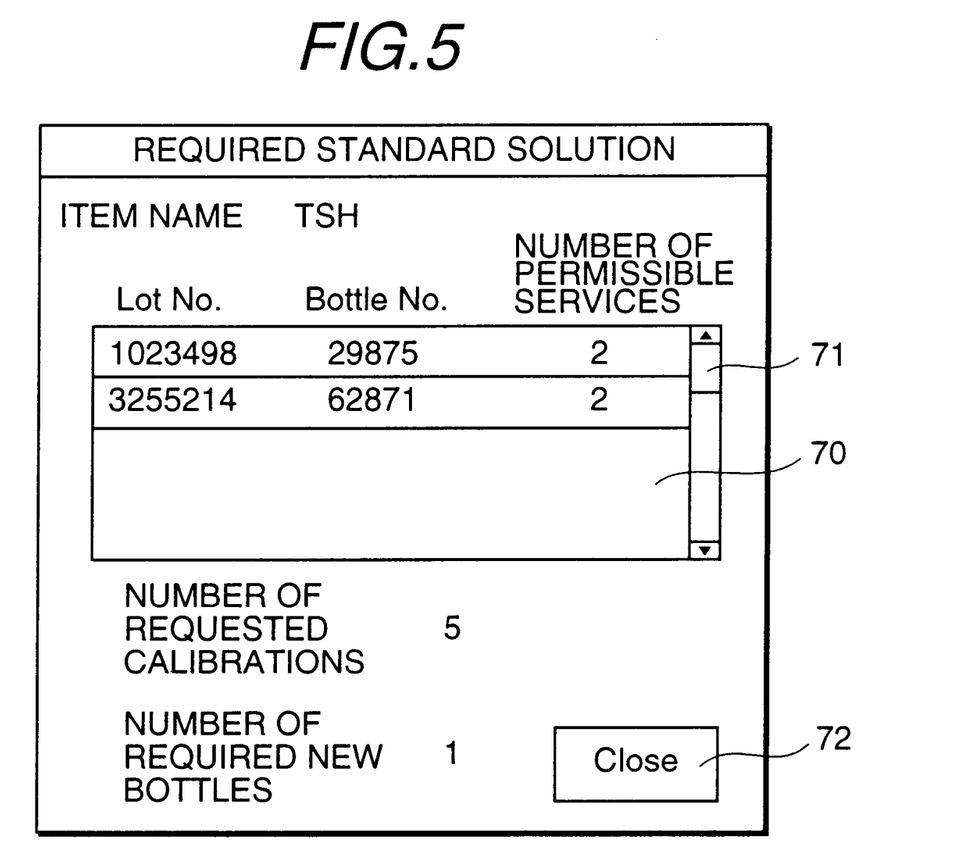
FIG. 5 shows an example of displaying the difference between the number of permissible services of the preset calibrator and the number of requested items.

In Step S7, the computer 11 compares the planned number of calibrations for each requested analysis item and the number of permissible services for each stored analysis item regarding the bottles on the rack, wherein this comparison is made for the same analysis items. In Step S8, said computer determines whether or not the number of permissible services is greater than the planned number of the requested calibrations. Namely, it checks for each analysis item to see if the calibrator solution on the rack is sufficient or not for subsequent use of calibrators. If said computer determines that the number of permissible services is greater for the analysis items to be calibrated, it goes to Step S11. If said computer draws a negative conclusion, namely, if it determines that the number of permissible services is insufficient for subsequent calibration, it goes to Step S9, and the screen as shown in FIG. 5 is indicated on display unit 19. In Step S9, the computer 11 calculates the difference between the number of permissible services and the number of requested analysis items, and indicates the information on the screen based on said calculation. Said screen displays the number of the new calibrator bottles to be added in order to secure the capacity of the calibrators required to satisfy the planned number of the calibrations.

FIG. 5 shows an example of displaying the difference between the number of permissible services of the calibrator samples and the number of requested items. Display on the display window 70 at the center in the vertical direction indicates the following: There are two calibrator samples located on one rack and registered as usable with respect to the analysis item of TSH, wherein the number of permissible services for calibration is 2 for the calibrator sample whose lot number is 1023498 and whose bottle number is 29875, and the number of permissible services for calibration is also 2 for the calibrator sample whose lot number is 3255214 and whose bottle number is 62871. The column for the number of requested calibrations positioned on the lower portion of the screen shows that the number of requested calibrations is 5. The column for required new bottles indicates that the number of calibrator bottles to be added is one; namely that the difference between the number of permissible services and the number of requested items is one in terms of the number of bottles. If the number of calibrator bottles is so great that said bottles cannot be displayed at one time, as in the case of analysis items requiring calibrations at multiple points, the display of the calibrator bottles can be changed sequentially by scrolling the screen by means of scroll bar 71 on the right of the display window 70. The screen given in FIG. 5 will disappear by pressing the CLOSE button 72.

In Step S10 shown in FIG. 4, additional calibrator bottles are loaded as required onto the rack to be read. In this case, the operator sets the required number of calibrator bottles on the rack according to the display on the screen given in FIG. 5. In the example of FIG. 5, the number of the bottles is only one. After Step S10 or in Step S11 if the result of decision in Step S8 is affirmative, the operator presses the Analysis Start button (Start button 122 in FIG. 6) to cause reaction between the calibrator sample and reagent, thereby generating reaction solution. To ensure that measurement and analysis can be performed for calibration of said reaction solution, calibrator sample bottles are automatically fed in conformity to the preset algorithm. For the multiple calibrator bottles with respect to the same analysis item, said algorithm can be created (1) in order of the term of validity (the earliest terms of validity first) when bottles are not yet opened, (2) in order of date (the earliest date first) when bottles are opened, or (3) in the ascending order of the remaining number of permissible calibrations. If said algorithm is created according to (1), the number of older bottles can be minimized. The number of the bottles past the term of validity can be minimized by following the order of (2), and the number of half-used bottles and deterioration thereof can be minimized by following the order of (3).

In Step S12, the result of calibration is output to display unit 19, and calibration terminates in Step S13.

FIG. 4 shows calibration prior to start of analysis. For analysis items using the reagent vulnerable to degeneration, calibration is performed halfway through the continuous analysis operations due to a great number of blood samples, similarly to the above-mentioned case. Furthermore, when measurement and analysis are performed for calibration in the multiple measuring channels using multiple calibrator samples, calibration is performed in parallel thereto.

As disclosed above, automatic control of the remaining number of calibrator samples relieves the operator of calculation and other related work, thereby reducing the operator load and avoiding errors. This will eliminate possible waste of high-priced calibrator samples due to errors and the time required to repeat the operation, and will effectively provide the results of error-free reliable analysis, without imposing undue labor on the operator.

FIG. 6 shows an example of the screen shown on the display unit 19. This screen is used to select and register the analysis item to be calibrated and the analysis unit to be used for calibration. The screen in FIG. 6 has a Routine operation tab 101, Reagent control tab 102, Calibration tab 103, Quality control tab 104 and Utility tab 105 arranged on the tab line of the top. A line showing the Status button 201 and Reference solution control button 202 is located immediately below the tab line. Display window 75 indicates the information which appears when Calibration tab 103 and Status button 201 have been selected.

The display window 75 at the center of the screen in the vertical direction indicates the item name (for calibrator sample analysis) column 106 and analysis unit (used for analysis) column 108 in that order as viewed from the left. The item name column 106 indicates all the analysis items to be calibrated. If the number of analysis items is so great that they cannot be displayed at one time, the display of the analysis items can be changed by scrolling the screen by means of scroll bar 111. The analysis unit column 108 indicates "IM" representing an immunological analysis unit or "P" showing a biochemical analysis unit where a pipetter method is used for dispensation. For example, let us consider the analysis unit when the analysis item name is TSH. This line indicates that reagent required to start calibration for the analysis item of TSH is set in the immunological analysis unit No.1 (IM1) and immunological analysis unit No.2 (IM2). Similar meaning is denoted in other lines.

Registration button 115 and Cancel button 116 are arranged on the bottom of the display window 75. If a line of the display window 75 is selected, and the Registration button 115 is pressed, that calibration for the analysis item shown on said line is performed by the analysis unit shown on said line is registered (stored). Said registration is canceled by pressing the Cancel button 116.

Stop button 117, Sample Stop button 118, Alarm button 119, Overview button 120, Print button 121 and Start button 122 are arranged in the vertical direction on the right of the screen illustrated in FIG. 6, as viewed from the top. The Stop button 117 is a button to terminate the analysis operation. The Sample Stop button 118 is pressed to stop sampling of the specimen. Pressing the Alarm button 119 will give indications showing the history of alarms. The Overview button 120 is utilized to observe the overview of the entire system. The Print button 121 is employed to start printing, and Start button 122 is pressed to initiate analysis.

Figure 7:
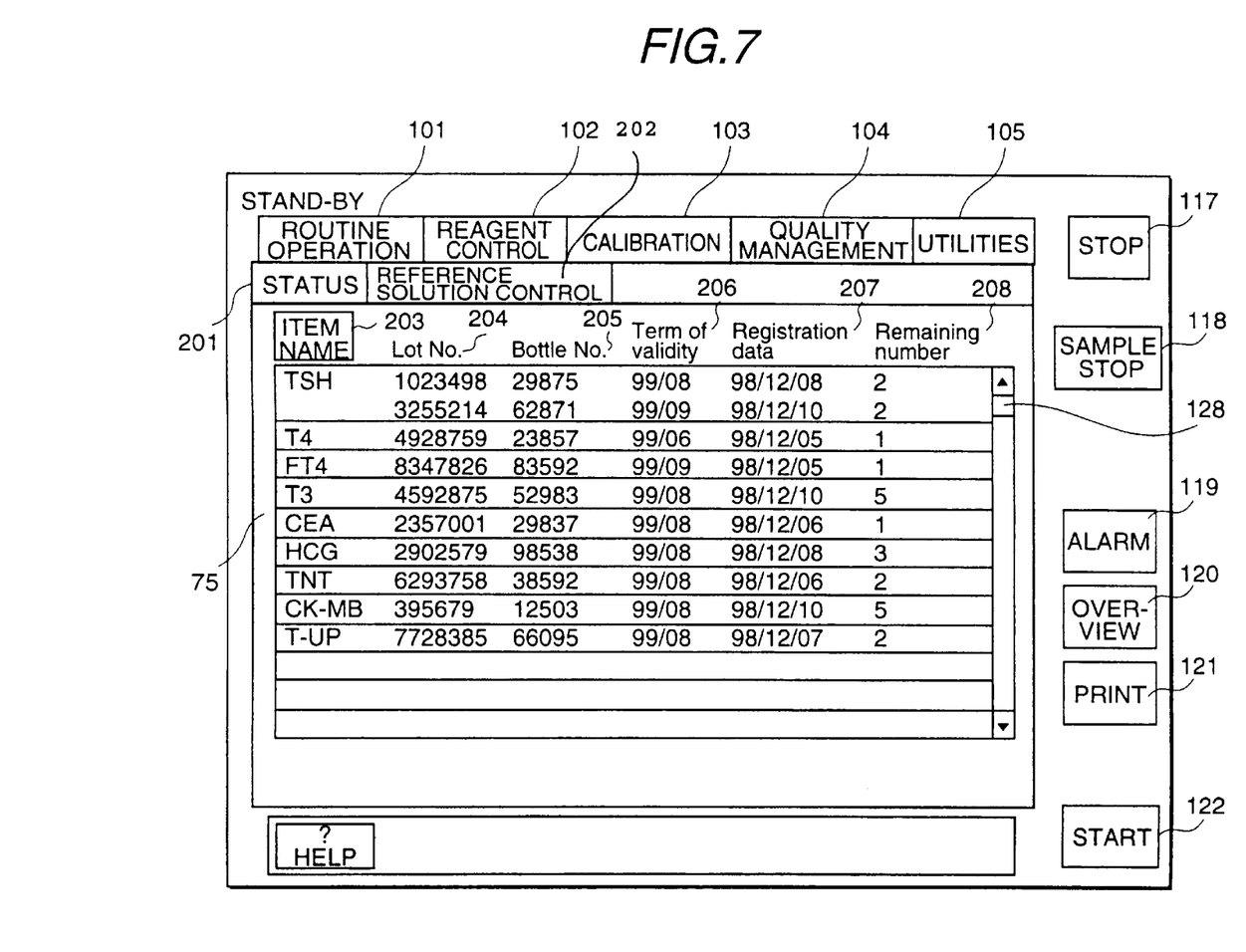
FIG. 7 shows an example of the screen used to display the number of permissible services provided by the calibrator sample.

FIG. 7 shows another example of the screen displayed on the display unit 19. It gives an example of the screen which appears when the Standard Solution Control switch 202 is selected. The reference solution is used in the same sense as the calibrator sample. This screen displays the current state of the calibrator samples registered so far wherein said calibrator samples are still valid and still have the number of permissible services, namely which can still be used. Display window 75 contains the item name (for calibrator sample analysis) column 203, lot number (for calibrator sample) column 204, bottle number (for calibrator sample) 205, the term of validity (for calibrator sample) 206, registration date (for calibrator sample) column 207, and remaining number (number of permissible calibrations of calibrator sample) column 208. If the number of analysis items is so great that they cannot be displayed at one time, the display can be changed sequentially by scrolling the screen by means of scroll bar 128.

In addition to calibration, the automatic analytical apparatus provides quality control by measuring the quality control samples of known concentration during measurements of many general specimens. The x-R control chart method is one of the typical methods for such measurements. This method measures quality control samples during routine examination, and checks the average value (x) and standard deviation (R) to determine if the examination is carried out correctly or not.

Figure 8:
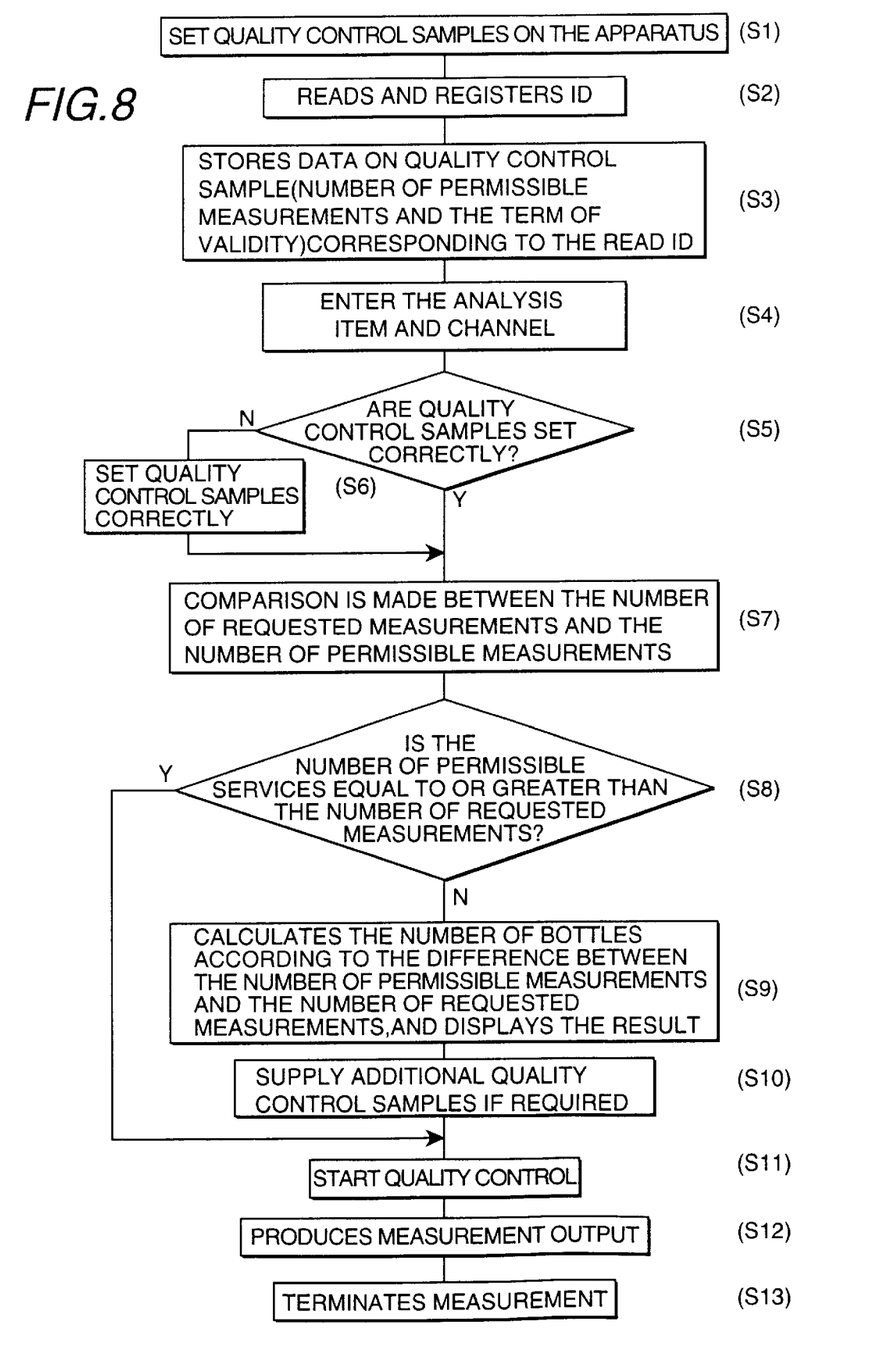
FIG. 8 is a flow chart representing the quality control operation procedure.

FIG. 8 shows an example of the flowchart representing the quality control operation procedure. Such a flowchart allows the remaining volume of the control samples to be checked automatically, and permits the operator to take necessary actions. The flowchart of FIG. 8 is substantially the same as that of FIG. 4, the difference being that the calibrator samples are replaced by quality control samples. Consequently, the description applies to FIG. 8 when the calibrator samples in said description is replaced by quality control samples, and the remaining number of permissible calibrations in the algorithm (3) explained with reference to Step S11 is replaced by the number of permissible measurements. Consequently, to avoid duplication, explanation of the flow of FIG. 8 will be omitted.

As disclosed above, automatic management of the remaining numbers of the calibrator samples and quality control samples relieves the operator of calculation and other related work, thereby reducing the operator load and avoiding errors. This will eliminate possible waste of high-priced calibrator samples due to errors and the time required to repeat the operation, and will effectively provide the results of error-free reliable analysis, without imposing undue labor on the operator.

What is claimed is:

1. A method for handling specific sample solutions including the steps of:
   (a) setting on a rack supply unit of an automatic analytical apparatus equipped with an analysis unit to analyze samples, a rack loaded with one or more specific bottles which contain specific sample solutions and which are respectively provided with identification information concerning the sample solutions, said solutions being used repeatedly for calibration or quality control;
   (b) storing into a memory device a number of permissible services for each analysis unit with regard to said specific sample solutions for all the specific bottles on said rack, based on reading of the identification information provided on said specific bottles on said rack;
   (c) determining whether or not an amount of said specific sample solutions on said rack is sufficient, based on a planned number of times that calibration or quality control is to be performed for each analysis item which is requested to a controller, and said number of permissible services;
   (d) displaying on a screen of a screen display unit the number of new specific bottles to be added to said rack in order to satisfy the planned number of times if said specific sample solutions are determined to be insufficient;
   (e) adding any new specific bottles to said rack which are required;
   (f) automatically transferring from said rack supply unit to said analysis unit said rack to which any new specific bottles have been added, and
   (g) performing calibration or quality control.

2. A method for handling specific solutions according to claim 1, said method further containing a step of displaying on said screen display unit the number of permissible services of the remaining solution for each specific bottle on said rack.

3. A method for handling specific solutions according to claim 1, said method further containing a step of selecting through the screen for selecting a combination of the types of analysis items and analysis units, said analysis unit where said rack is transferred.

4. A method for handling specific sample solutions including the steps of:
   (a) setting on a rack supply unit of an automatic analytical apparatus equipped with an analysis unit to analyze samples, a rack loaded with one or more specific bottles which contain specific sample solutions and which are respectively provided with identification information concerning the sample solutions said solutions being used repeatedly for calibration or quality control;
   (b) storing into a memory device a number of permissible services for each analysis system with regard to said specific sample solutions for all the specific bottles on said rack, based on reading of the identification information provided on said specific bottles on said rack;
   (c) determining whether or not an amount of said specific sample solutions on said rack is sufficient, based on a planned number of times that calibration or quality control is to be performed for each analysis item which is requested to a controller, and said number of permissible services;
   (d) displaying on a screen of a screen display unit the number of new specific bottles to be added in order to satisfy the planned number of times if said specific sample solutions are determined to be insufficient;
   (e) automatically transferring from said rack supply unit to said analysis unit said rack where new bottles are added, and performing calibration or quality control; and
   (f) managing a term of validity subsequent to opening of said bottles, by treating a time point when said bottles are opened as a time when the identification information on said first bottle has been read, in a case that the specific bottle set on said rack supply unit is a first bottle not registered previously.

* * * * *